US008585894B1

(12) United States Patent
Uselius

(10) Patent No.: US 8,585,894 B1
(45) Date of Patent: Nov. 19, 2013

(54) CHROMATOGRAPHY COLUMN NOZZLE

(71) Applicant: GE Healthcare Bio-Sciences AB, Uppsala (SE)

(72) Inventor: Per Uselius, Uppsala (SE)

(73) Assignee: GE Healthcare Bio-Sciences AB, Uppsala (SE)

( * ) Notice: Subject to any disclaimer, the term of this patent is extended or adjusted under 35 U.S.C. 154(b) by 0 days.

(21) Appl. No.: 13/683,199

(22) Filed: Nov. 21, 2012

(51) Int. Cl.
*B01D 15/08* (2006.01)

(52) U.S. Cl.
USPC .......................... 210/198.2; 210/281; 210/656

(58) Field of Classification Search
USPC ................... 210/656, 659, 198.2, 281; 95/82; 96/101, 103
See application file for complete search history.

(56) References Cited

U.S. PATENT DOCUMENTS

| | | | | |
|---|---|---|---|---|
| 5,902,485 A * | 5/1999 | Davis et al. | .................... | 210/656 |
| 6,277,283 B1 * | 8/2001 | Davis et al. | .................... | 210/656 |
| 7,972,506 B2 * | 7/2011 | Hofmann | .................... | 210/198.2 |
| 2008/0164210 A1 * | 7/2008 | DeMarco | ...................... | 210/656 |
| 2008/0217248 A1 * | 9/2008 | Gebauer | ........................ | 210/656 |
| 2008/0272045 A1 * | 11/2008 | Andersson et al. | ......... | 210/198.2 |
| 2010/0189602 A1 * | 7/2010 | Baeuerle et al. | ................ | 422/70 |
| 2010/0276370 A1 * | 11/2010 | Davis et al. | .................... | 210/656 |

* cited by examiner

*Primary Examiner* — Ernest G Therkorn

(57) ABSTRACT

A nozzle assembly (1) provided in a chromatography column (3), said nozzle assembly comprising a nozzle tube (21) through which chromatography media slurry is to be provided to the column (3). According to the invention said nozzle assembly (1) further comprises a pivot (39) connected in a first end (40*a*) to a pivot point arm (35), said pivot (39) can be pivoted into at least two different locked pivot positions and said pivot (39) being connected to the nozzle tube (21) such that a nozzle tip (25) of said nozzle tube is adjusted into at least two different locked nozzle tip positions corresponding to the at least two different locked pivot positions.

7 Claims, 5 Drawing Sheets

CHROMATOGRAPHY COLUMN NOZZLE

FIELD OF THE INVENTION

The present invention relates to a nozzle assembly provided on a chromatography column.

BACKGROUND OF THE INVENTION

Chromatography columns are typically comprised of a column tube with a top end cell covering the top opening of the tube and a bottom end cell covering the bottom opening of the tube. A chromatography column with variable column height also comprises a plunger or adaptor integrated in the top end cell, which adaptor can be moved to different heights within the column tube. The top end cell (possibly integrated with an adaptor) and bottom end cell comprise further a nozzle assembly adapted to provide chromatography media to the column, sample inlet/outlet, sample distribution means, filter, net, O-rings and seals. The nozzle assembly comprises typically a nozzle tube through which chromatography media in the form of a slurry is provided to the column. The nozzle assembly comprises further normally a slurry outlet used during the unpacking of the column. In U.S. Pat. No. 5,902,485 an access valve suitable for controlling fluid flow into and out of a chromatography column is described. Axial movement of the probe, also known as a nozzle tube, adjusts the valve between a fully open condition, in which both a first conduit extending through the probe and a second conduit defined around the probe are open to the column interior, and a partly open condition in which a sealing component of the probe closes the second conduit. Also further axial movement of the probe provides a fully closed position in which both conduits are closed. The partly open position is useful for packing chromatography media into its column while the third position is useful for unpacking the same.

The movement of the probe into the three different positions is crucial and important. In prior art this is sometimes difficult and not very exact. Some solutions are also rather expensive and require complicated mechanics. In U.S. Pat. No. 5,902,485 one possible way of performing this is shown. In this described system the axial movement of the nozzle tip is performed by use of a screwing mechanism which will not provide very exact positions.

SUMMARY OF THE INVENTION

An object of the invention is to provide a means for facilitating the controlling of the nozzle tube.

A further object of the invention is to provide an accurate and easy to handle means for controlling the positions of the nozzle tube.

A further object of the invention is to provide a cheap solution comprising few parts for the controlling of the nozzle tube.

A further object of the invention is to improve accuracy of the nozzle tube positions and to improve convenience for the operator during operation.

This is achieved in a nozzle assembly according to claim 1.

Hereby, a nozzle assembly is achieved providing at least two easily entered distinct positions for the nozzle tube. The nozzle assembly comprises few parts and is cheap to produce. The nozzle tip will be provided in exact positions and the operator needs not to do any further adjustments or controlling to adjust position.

Suitable embodiments are described in the dependent claims.

DETAILED DESCRIPTION OF THE INVENTION

Figure 1:
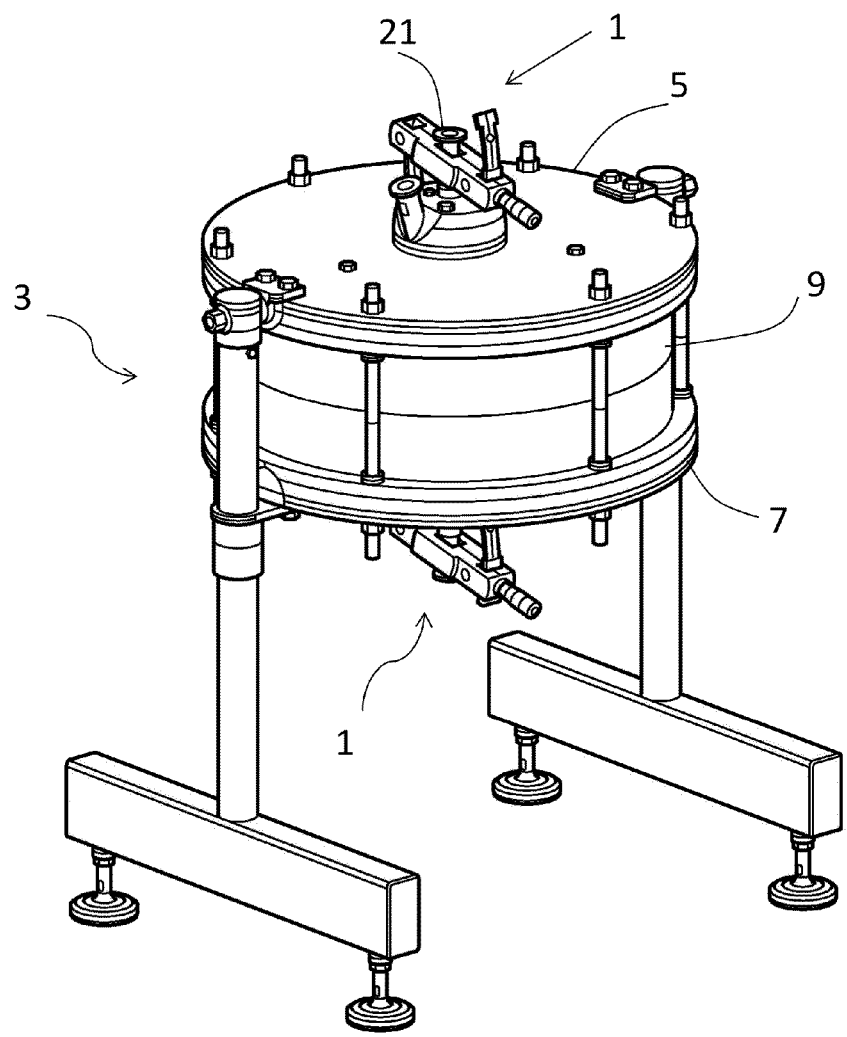
FIG. 1 shows one embodiment of a nozzle assembly provided on a chromatography column according to the invention.

FIG. 1 shows one embodiment of a nozzle assembly 1 provided on a chromatography column 3 according to the invention. Actually one nozzle assembly 1 according to the invention is provided on a top end cell 5 of the chromatography column 3 and another nozzle assembly 1 according to the invention is provided on a bottom end cell 7 of the chromatography column 3. A column tube 9 is provided in between the top end cell 5 and the bottom end cell 7. Here a chromatography column without movable adaptor is shown. The invention is however also applicable to a chromatography column having a movable adaptor.

The nozzle assembly 1 comprises a nozzle tube 21 protruding through the top or bottom end cell 5, 7. Chromatography media in the form of a slurry is to be entered into the column 9 through the nozzle tube 21. The nozzle assembly 1 comprises further controlling means 31 for controlling the nozzle tube 21 to protrude into the column or not. This will be further described in relation to FIGS. 2-4.

Figure 2A:
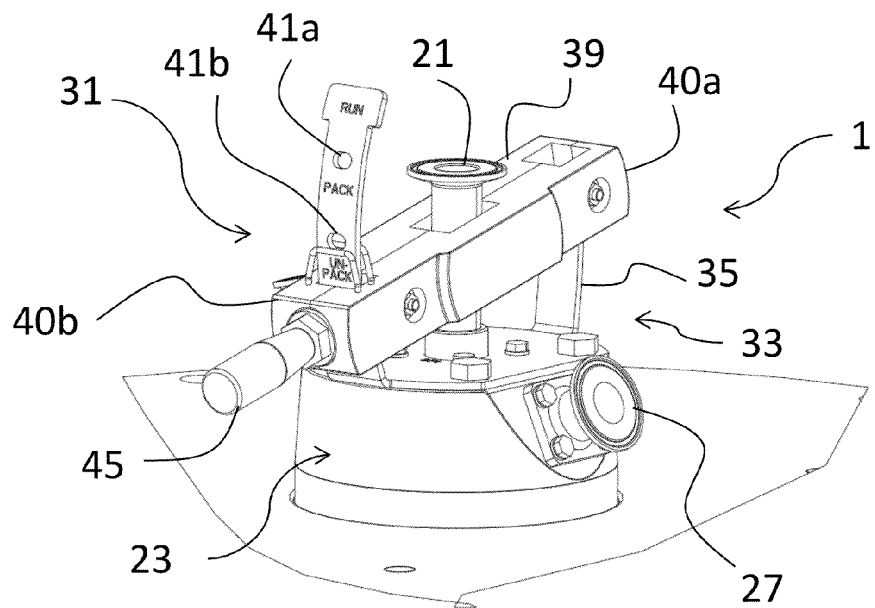
FIGS. 2a and 2b show the same nozzle assembly as in FIG. 1 in more detail and in two different angles.
Figure 2B:
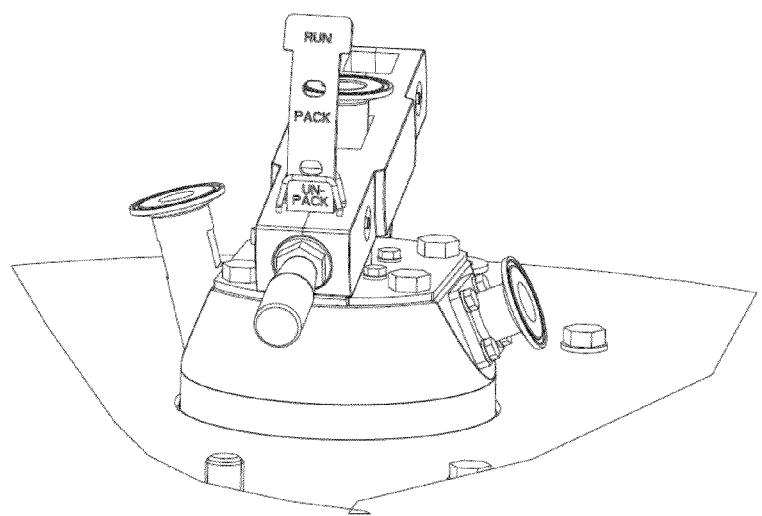
Figure 3:
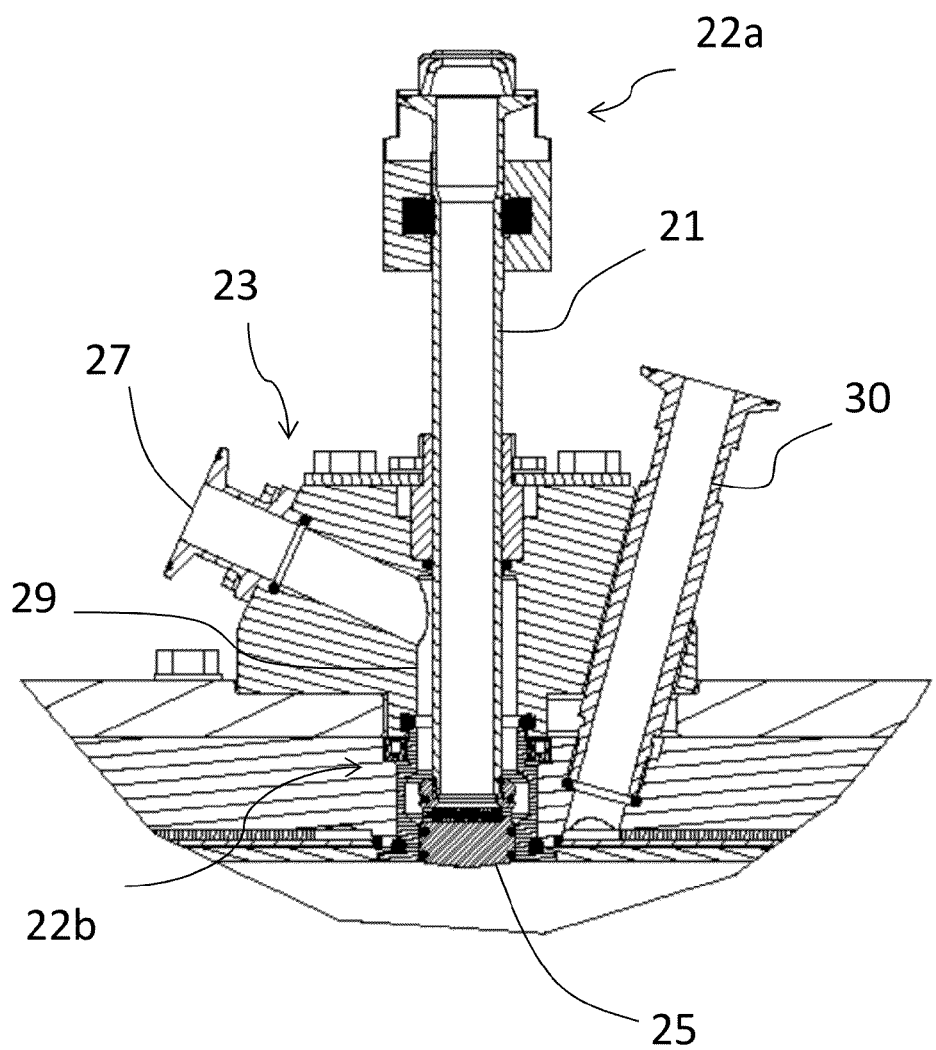
FIG. 3 shows in cross section another view of the nozzle assembly.

FIGS. 2a-2b shows the same nozzle assembly 1 as in FIG. 1 in more detail and in two different angles. The nozzle assembly 1 comprises a nozzle body 23 through which the nozzle tube 21 protrudes into the column. This can be seen in FIG. 3. The nozzle tube 21 is elongated and comprises a first end 22a pointing out from the chromatography column when the nozzle assembly 1 is attached to the chromatography column and a second end 22b entering into the column tube 9 in at least one of its positions, said second end 22b comprising a nozzle tip 25 through which chromatography media slurry is to be provided into the column.

The nozzle assembly further comprises a slurry outlet 27. The slurry outlet 27 protrudes through the nozzle body 23, whereby the angle between the nozzle tube 21 and the slurry outlet 27 is more than 0 degrees and less than 90 degrees. Inside the nozzle body 23 the slurry outlet 27 hits the nozzle tube 21 and at that point the slurry outlet 27 enters into a second part 29 of the slurry outlet that is surrounding the second end 22b of the nozzle tube 21. The second part 29 of the slurry outlet is connected to one part of the nozzle tip 25. This will be further described in relation to FIGS. 4a-4c.

In this embodiment a mobile phase inlet 30 is provided separate from the nozzle tube 21. However the mobile phase inlet 30 protrudes through the nozzle body 23 but is separated from the nozzle tube 21 and the slurry outlet 27. This is suitable because it will provide a more simple construction requiring less O-rings and thereby being less susceptible to leakage compared to a solution where the mobile phase inlet is centred around the nozzle tube.

The nozzle assembly 1 comprises further a controlling means 31 for controlling the nozzle tube 21 to protrude into the column or not. This controlling means 31 comprises in one embodiment of the invention a pivot base plate 33 attached to the nozzle body 23. The nozzle tube 21 is protruding through essentially the center of the pivot base plate 33. Said pivot base plate 33 comprises at opposite sides of its periphery two essentially perpendicularly extending arms, one arm being a pivot point arm 35 to which a first end 40*a* of a pivot 39 is permanently secured and the other arm being a pivot positions arm 37 to which a second end 40*b* (the opposite to the first end 40*a*) of the pivot 39 can be attached in at least two different locked pivot positions. The pivot positions arm 37 comprises in this shown embodiment three holes 41*a*, 41*b*, 41*c* into which a spring loaded pin 43 controlled by a handle 45 provided at the second end 40*b* of the pivot 39 can be introduced and thereby locking the pivot 39 in one of the three positions.

The nozzle tube 21 is connected to the pivot 39 at about the middle of the pivot. Hereby the nozzle tip 25 is displaced into three different nozzle tip positions corresponding to the three different pivot positions. These three nozzle tip positions will be further described in relation to FIGS. 4*a*-4*c* below.

Figure 4A:
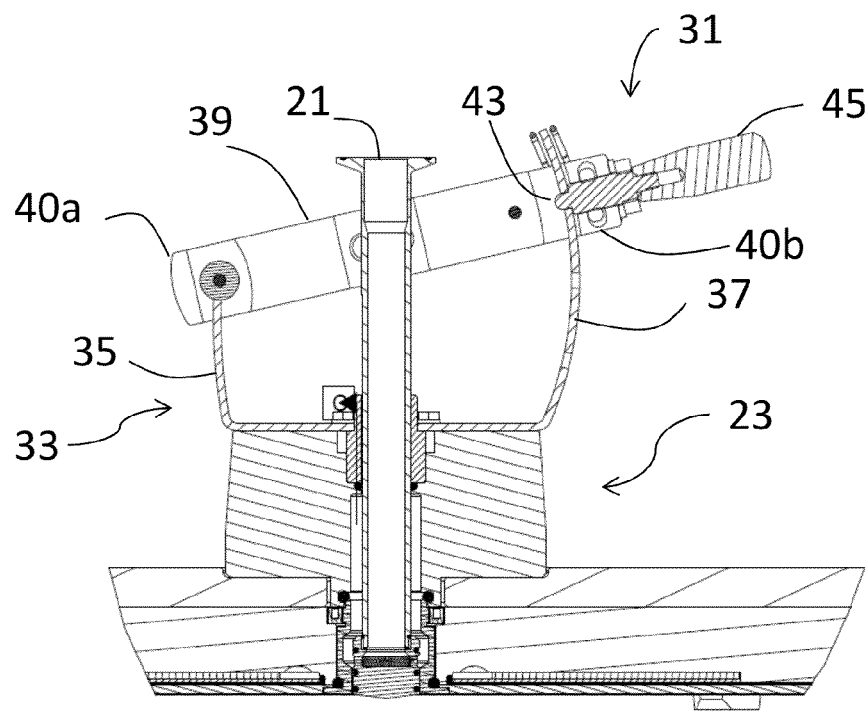
FIGS. 4a-4c show the same nozzle assembly as in FIG. 1 in cross section in the three different positions according to the invention.

The pivot base plate is in this shown embodiment provided as one piece comprising the two arms 35, 37—see FIG. 4*a*. However an alternative would be to attach two separate arms to the nozzle body 23. Furthermore, the pivot point arm 35 could be provided as adjustable in axial direction in order to further improve the precision for the positioning of the nozzle tip.

Figure 4B:
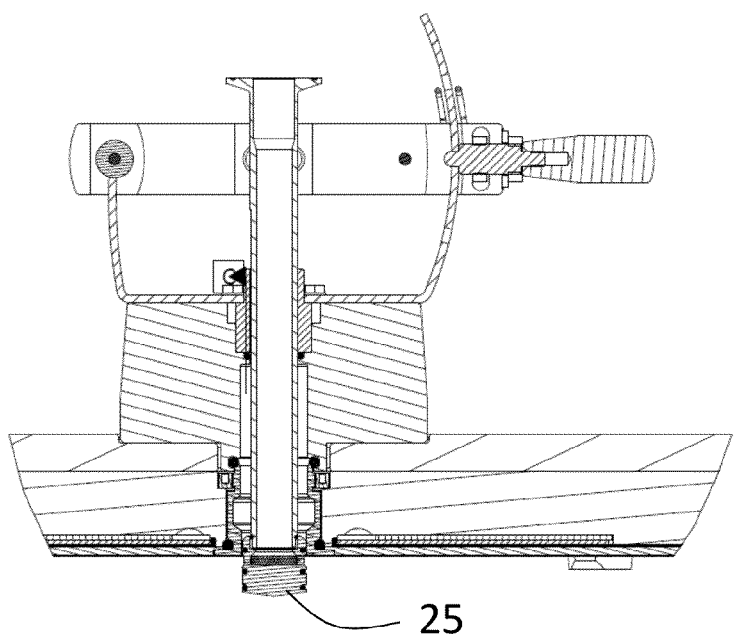
Figure 4C:
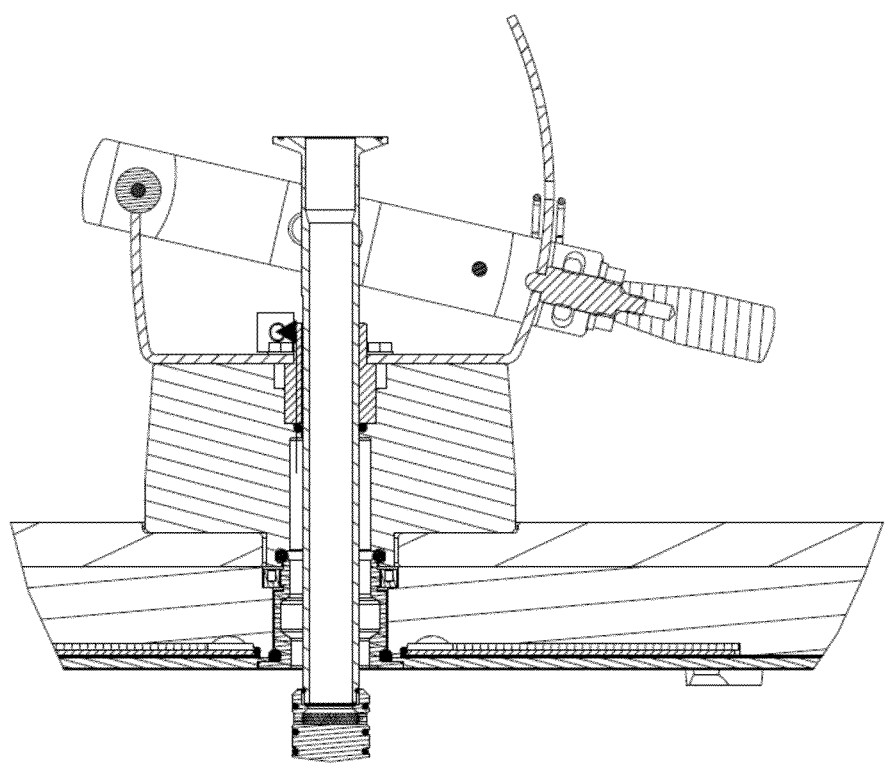

FIGS. 4*a*-4*c* shows the same nozzle assembly as in FIG. 1 in cross section in the three different positions according to the invention. A run position is shown in FIG. 4*a*. This position is used during chromatography when neither the nozzle tube 21 nor the slurry outlet 27 should communicate with the column interior. In this position the nozzle tip 25 is in its most retracted position, i.e. not protruding into the column. Seals are provided around the nozzle tip such that there is no opening between the column and the nozzle tube. The run position corresponds to the handle and the spring loaded pin 43 being in its uppermost position with the pin 43 locked in the uppermost hole 41*a* (referring up as a direction in the FIG. 4*a*. However the nozzle assembly is also provided in the opposite direction at the bottom part of the column).

A pack position is shown in FIG. 4*b*. In this position the nozzle tip 25 is partly introduced inside the column. This position corresponds to the handle 45 and the spring loaded pin 43 being in the middle position, i.e. the spring loaded pin 43 locked in the middle hole 41*b*. In this position the nozzle tip 25 prevents any connection between the column interior and the slurry outlet 27 and admits communication between the column interior and the nozzle tube 21. Hereby slurry can be introduced through the nozzle tube 21 into the column.

An unpack position is shown in FIG. 4*c*. In this position the nozzle tip 25 is completely introduced inside the column. This corresponds to the handle 45 and the spring loaded pin 43 being in its lowermost position and the spring loaded pin 43 being locked in the lowermost hole 41*c* (referring to directions in the drawing). In this position the nozzle tip 25 admits a connection between the column interior and the slurry outlet as well as a connection between the nozzle tube 21 and the column interior. Hereby slurry can be withdrawn through the slurry outlet 27 and the column can be unpacked.

Even though the present invention has been described above in terms of specific embodiments, many modification and variations of this invention can be made as will be obvious to those skilled in the art, without departing from its spirit and scope as set forth in the following claims.

What is claimed is:

1. A nozzle assembly (1) provided in a chromatography column (3), said nozzle assembly comprising a nozzle tube (21) through which chromatography media slurry is to be provided to the column (3), wherein said nozzle assembly (1) further comprises a pivot (39) connected in a first end (40*a*) to a pivot point arm (35), said pivot (39) can be pivoted into at least two different locked pivot positions and said pivot (39) being connected to the nozzle tube (21) such that a nozzle tip (25) of said nozzle tube is adjusted into at least two different locked nozzle tip positions corresponding to the at least two different locked pivot positions.

2. The nozzle assembly of claim 1, wherein said nozzle tube (21) is elongated and comprises a first end (22*a*) pointing out from the chromatography column (3) when the nozzle assembly (1) is attached to the chromatography column and a second end (22*b*) entering into the column (3) in at least one of said pivot positions, said second end (22*b*) comprising the nozzle tip (25) through which chromatography media slurry is to be provided into the column.

3. The nozzle assembly of claim 2, further comprising a slurry outlet (27) through which chromatography media can be removed from the chromatography column (3), said slurry outlet (27) at least partly surrounds the second end (22*b*) of the nozzle tube (21) and communicates with the nozzle tip (25).

4. The nozzle assembly of claim 3, wherein said pivot (39) can be pivoted into three different locked pivot positions, thereby providing the nozzle tip (25) in corresponding three different locked nozzle tip positions, a run position which corresponds to the nozzle tip (25) being retracted from the column (3) and both nozzle tube (21) and slurry outlet (27) being closed towards the interior of the column (3), a pack position which corresponds to the nozzle tip (25) being partly introduced into the column (3) and thereby opening the connection to the nozzle tube (21) but not to the slurry outlet (27) and an unpack position which corresponds to the nozzle tip (25) being completely introduced into the column (3) and thereby opening the connection to both the nozzle tube (21) and the slurry outlet (27).

5. The nozzle assembly of claim 1, further comprising a pivot base plate (33) attached to a nozzle body (23) which is provided around a part of the nozzle tube (21) and the slurry outlet (27) and is attached to the column (3), said pivot base plate (33) comprising at opposite sides of its periphery two essentially perpendicularly extending arms (35, 37), one arm being the pivot point arm (35) to which a first end (40*a*) of the pivot (39) is permanently secured and the other arm being a pivot positions arm (37) to which a second end (40*b*) of the pivot (39) can be attached in at least two different locked positions.

6. The nozzle assembly of claim 5, wherein the pivot positions arm (37) comprises three holes (41*a*, 41*b*, 41*c*) into which a spring loaded pin (43) controlled by a handle (45) provided at the second end (40*b*) of the pivot (39) can be introduced and thereby locking the pivot (39) in one of the three positions.

7. The nozzle assembly of claim 1, wherein the nozzle tube (21) is connected to the pivot (39) at about the middle of the pivot.

* * * * *